(12) United States Patent
Laurent et al.

(10) Patent No.: US 9,060,985 B2
(45) Date of Patent: Jun. 23, 2015

(54) USE OF ROSMARINIC ACID AND THE DERIVATIVES THEREOF TO TREAT CIGUATERA

(75) Inventors: Dominique Laurent, Asson (FR); Serge Pauillac, Palaiseau (FR); Mireille Chinain, Tahiti (FR); Taiana Darius, Tahiti (FR); Shilpa Kumar-Roine, New Caledonia (FR)

(73) Assignees: INSTITUT DE RECHERCHE POUR LE DEVELOPPEMENT, Marseille (FR); INSTITUT LOUIS MALARDE, Papeete (PF)

( * ) Notice: Subject to any disclaimer, the term of this patent is extended or adjusted under 35 U.S.C. 154(b) by 112 days.

(21) Appl. No.: 13/388,029

(22) PCT Filed: Jul. 21, 2010

(86) PCT No.: PCT/FR2010/000527
§ 371 (c)(1),
(2), (4) Date: Apr. 13, 2012

(87) PCT Pub. No.: WO2011/012780
PCT Pub. Date: Feb. 3, 2011

(65) Prior Publication Data
US 2012/0196929 A1    Aug. 2, 2012

(30) Foreign Application Priority Data
Jul. 31, 2009   (FR) .................................. 09 03781

(51) Int. Cl.
*A61K 31/216* (2006.01)
*A61P 1/00* (2006.01)
*A61P 25/00* (2006.01)
*A61P 9/00* (2006.01)
*A61P 21/00* (2006.01)

(52) U.S. Cl.
CPC .................................. *A61K 31/216* (2013.01)

(58) Field of Classification Search
None
See application file for complete search history.

(56) References Cited

U.S. PATENT DOCUMENTS

2005/0148539 A1    7/2005   Baden ......................... 514/450

FOREIGN PATENT DOCUMENTS

WO    WO 2005/027903    3/2005

OTHER PUBLICATIONS

Aung, Rosmarinic acid in *Argusia argentea* inhibits snake venom-induced hemorrhage, Journal of Natural Medicines, pub. date of May 29, 2010, 64, pp. 482-486.*
Poli, Identification of Caribbean Ciguatoxins As the Cause of an Outbreak of Fish Poisoning Among U.S. Soldiers in Haiti, Toxicon, 1997, 35(5), pp. 733-741.*
Triantaphyllou, Antioxidative properties of water extracts obtained from herbs of the species *Lamiaceae*, Int. J. of Food Sciences and Nutrition, 2001, 52, pp. 313-317.*
Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
Benoit et al., *Cybium.* 24(3): 33-40, 2000.
Bourdelais et al., *J Nat Prod.* 68(1): 2-6, 2005.
Bourdelais et al., *Cell Mol Neurobiol.* 24(4): 553-563, 2004.
Boydron-Le Garrec et al., *Toxicon.* 46(6): 625-634, 2005.
Friedman, M., et al., *Marine Drugs.* 6(3): 456-479, 2008.
Hamilton, B., et al., *Toxicon.* 40: 685-693, 2002.
Lewis, R.J., et al., *J Am Chem Soc.* 120: 5914-5920, 1998.
Mattei et al., *Cells. PLoS ONE* 3(10): 1-9, 2008.
Murata, M, et al., *J Am Chem Soc.* 111: 8929-8931, 1989.
Regus, R. *Anales de la Real Acad de Farmacia.* 66(3): 433-447, 2000.
Sauviat, M.P., et al., *Blood Cells Mol & Diseases.* 36(1): 1-9, 2006.
International Search Report in PCT/FR2010/000527 issued Sep. 22, 2010.

* cited by examiner

*Primary Examiner* — San-Ming Hui

*Assistant Examiner* — Andrew Lee (74) *Attorney, Agent, or Firm* — Norton Rose Fulbright US LLP (57) ABSTRACT

The present invention relates to rosmarinic acid and to the derivatives thereof, expressed by the compounds of general formula (I), for the use thereof to prevent and/or treat disorders caused by ciguatoxin poisoning and for preparing a pharmaceutical composition for preventing and/or treating disorders caused by ciguatoxin poisoning.

8 Claims, 1 Drawing Sheet

Figure 1

Figure 2

USE OF ROSMARINIC ACID AND THE DERIVATIVES THEREOF TO TREAT CIGUATERA

This application is a national phase application under 35 U.S.C. §371 of International Application No. PCT/FR2010/000527 filed 21 Jul. 2010, which claims priority to French Application No. 09/03781 filed 31 Jul. 2009. The entire contents of each of the above-referenced disclosures is specifically incorporated herein by reference without disclaimer.

The present invention relates to the use of rosmarinic acid and the derivatives thereof to manufacture a medicinal product intended for treating food poisoning by fish, in particular ciguatera.

Ciguatera is a form of ichthyosarcotoxism, i.e. a food poisoning by the flesh of fish contaminated with ciguatoxins (CTX) of the benthic microalga *Gambierdiscus* spp present in coral reefs.

It is one of the commonest forms of poisoning from fish in the regions of the Pacific, the Indian Ocean and the Caribbean.

The ciguatoxins enter the food chain via fishes browsing on coral and herbivores browsing on algae on which *Gambierdiscus toxicus* are attached. These fishes are then the prey of omnivorous fishes and then carnivores; the toxins are thus accumulated along the food chain. Among the 400 species potentially infected, the large predator fishes such as the barracuda, moray, grouper or also the jack are the most likely to cause poisoning.

The ciguatoxins are thermally stable, fat-soluble polyethers, of low molecular weight, and they are among the most powerful marine biotoxins, since just one microgram is enough to kill a person.

The techniques of chromatographic purification and detection have enabled 39 different ciguatoxins to be isolated. They vary according to their geographic origin (23 Pacific ciguatoxins or P-CTX, 12 Caribbean ciguatoxins or C-CTX and 4 Indian Ocean ciguatoxins or I-CTX), according to the fish species and according to their position in the food chain. Not all of their molecular structures have been elucidated.

The ciguatoxins are neurotoxins, whose action on the voltage-dependent sodium channels is responsible for the clinical manifestations observed in intoxication. The CTX act by keeping the sodium channels open at voltage values where normally they ought to be closed, leading to spontaneous and repetitive appearance of action potentials. The opening of the sodium channels is responsible for a massive influx of sodium ions into the cell, leading to swelling; this phenomenon is particularly visible at the Ranvier nodes and the axon terminals.

The nervous manifestations therefore result from this action of the toxins, both on the motor and sensory nerves and on the neuromotor junctions. The cardiac and digestive manifestations of the disease are also dependent on the action of the ciguatoxins on the sympathetic and parasympathetic nervous system.

"Ciguatoxins" denote, in particular, the Pacific ciguatoxins or P-CTX-1 to 23 of type 1 (Murata et al. 1989. *J. Am. Chem. Soc.* 111: 8929-31):

and of type 2 (Satake et al. 1993. *Tetrahedron Letter.* 34: 1975-78):

the Caribbean ciguatoxins or C-CTX-1 to 12 (Lewis et al. 1998. *J. Am. Chem. Soc.* 120: 5914-20):

and the Indian Ocean ciguatoxins or I-CTX-1 to 4 (Hamilton et al. 2002. Toxicon 40: 685-93).

There is at present no treatment for ciguatera; western medicine only offers medications for relieving the symptoms: antiemetics and antidiarrheal agents for gastrointestinal disorders; antihistamines against pruritus and analgesics for musculoskeletal disorders.

Mannitol is a compound that has been investigated for treatment of ciguatera; administered 48 to 72 hours after intoxication, mannitol is described as being capable of alleviating neurological and muscular disorders (Palafox et al., 1988, JAMA 259, 2740-2742; Blythe et al., 1994, Mem. Queensl. Mus. 34, 465-470). Clinical trials conducted blind with mannitol and a saline solution did not, however, show a beneficial effect of mannitol on the symptoms of ciguatera after 24 hours (Schnorf et al. 2002, Neurol. 58, 1155-1163); its efficacy is therefore controversial.

Two products are currently under investigation for the treatment of ciguatera:

two anticiguatoxin monoclonal antibodies, simultaneous administration of which neutralizes the action of ciguatoxin C-TX3C in vitro and in vivo (Inoue et al.; 2009, Toxicon doi: 10.1016/j.toxicon.2009.02.17);

brevenal, isolated from the brevetoxin-producing dinoflagellate *Karenia brevis* (Bourdelais et al., 2005, J. Nat Prod. 68(1), 2-6):

[Chemical structure of Brevenal]

Brevenal

It is a powerful inhibitor of the neurotoxic effects induced by the ciguatoxins and a potential treatment for ciguatera (Bourdelais et al., 2004 Molecular Neurobiology, 24(4), 553-563; Mattei et al., 2008, cells. PLoS ONE 3(10) 1-9). However, this compound is difficult to synthesize and can only be obtained in small amounts from cultures of *Karenia brevis*.

The traditional pharmacopoeia is richer in remedies than western medicine: in the Pacific, numerous traditional remedies based on plants are used for treating ciguatera.

Ethno-pharmacological surveys conducted principally in New Caledonia and on Vanuatu made it possible to draw up a list of nearly a hundred plants used in traditional medicine (Bourdy et al., 1992, J. Ethnopharmacology 36, 163-174; Laurent et al., 1993, ORSTOM Editions, Paris, pp. 51-116). In New Caledonia, the use of these remedies is extremely popular and the majority of the population prefer to go to healers rather than consult doctors. Among these remedies, the decoction of leaves of *Heliotropium foertherianum* Diane & Hilger is widely used in many islands of the South Pacific (New Caledonia, French Polynesia, Vanuatu, Tonga, Micronesia) and even in the Ryukyu islands of Japan. According to a survey conducted among the population of Noumea, more than 40% of the 500 persons questioned use this plant as treatment (Amade & Laurent, 1992, eds Gopalakrishnakone P. and Tan C. K., 2, 503-508).

Widely used in Polynesia, Micronesia and Melanesia and also present in the Indian Ocean, *Heliotropium foertherianum* is a coastal plant of the family Boraginaceae. Originally called *Tournefortia argentea* L.f., it was then called *Argusia argentea* (L.f.) Heine and remained under this name until recently when it was renamed *Tournefortia* before being called *Heliotropium* in 2003 after molecular studies. It also has been listed under the scientific names *Messerschmidia argentea* (L.f.) Johnston, *T. arborea* Blanco, *T. sarmentosa* sensu Christian non Lam. and *T. sericea* Cham.

Studies in vivo and in vitro on extracts of leaves of *Heliotropium foertherianum* have demonstrated the efficacy of this plant for combating the symptoms of ciguatera. Evaluated in a test of weight loss of mice intoxicated by moray liver containing ciguatoxins, the extract of leaves of *H. foertherianum* caused a decrease of the body weight reduction that had been induced (Amade & Laurent, 1992). This extract also showed effects identical to mannitol on isolated frog axons treated with Pacific ciguatoxin. In fact, this extract inhibits the spontaneous and repetitive discharges of action potentials caused by blocking of the sodium channels in the open position by the ciguatoxins and the resultant reentry of sodium. It also inhibits the swelling of the Ranvier nodes of the myelinated axons caused by the reentry of water corresponding to the osmotic change (Benoit et al., 2000, Cybium 24, 33-40). *H. foertherianum* also inhibits the swelling of human or frog erythrocytes caused by the ciguatoxin (Boydron et al., 2001, Rencontres en toxinologie: Explorer, exploiter les toxines et maitriser les organismes producteurs, Editions scientifiques et medicales Elsevier, Paris, pp. 63-6 and Boydron et al., 2002, Rencontres en toxinologie: Toxines et recherches biomédicales, Editions scientifiques et medicales Elsevier, Paris, pp. 101-104).

Next, using murine neuroblastomas (neuro-2a), it was shown that the extracts of leaves of this plant exerted a protective effect against the cytotoxic action of ciguatoxins and brevetoxins (Boydron-Le Garrec et al., 2005, Toxicon 46, 625-634). The brevetoxins belong to another class of marine biotoxins that resemble the ciguatoxins in their polyether structure and bind to the same site of the voltage-dependent sodium channels.

The inventors conducted research on *H. foertherianum* with the aim of identifying the substance that is able to combat the symptoms of the ciguatoxins.

Starting from a preparation of the remedy according to the method usually employed (Laurent et al., 1993): 200 grams of yellowed leaves are boiled in 1 liter of water for 30 minutes, the inventors isolated the active principle of *H. foertherianum* by bioguided chemical fractionation.

Structural analysis of the product is performed by proton and carbon NMR and mass spectrography; this led to identification of rosmarinic acid.

The present invention thus relates to the compounds of general formula (I):

[Chemical structure of formula (I)]

(I)

in which:

$R_1$ to $R_{10}$ represent, independently of one another:

a hydrogen atom or a halogen atom;

a $C_1$-$C_6$ alkyl radical, a $C_2$-$C_6$ acyl radical or a $C_3$-$C_{10}$ aryl radical;

a radical —O—$Z_1$ with $Z_1$ selected from the group comprising a hydrogen atom, a $C_1$-$C_6$ alkyl radical, a $C_2$-$C_6$ acyl radical, a $C_3$-$C_{10}$ aryl radical and a glycosyl radical;

a radical —S—$Z_2$ with $Z_2$ selected from the group comprising a hydrogen atom and a $C_1$-$C_6$ alkyl radical;

a radical with $Z_3$ and $Z_4$ selected, independently of one another, from the group comprising a hydrogen atom, an oxygen atom, a nitrogen atom, a $C_1$-$C_6$ alkyl radical, a $C_2$-$C_6$ acyl radical, a $C_3$-$C_{10}$ aryl radical and a glycosyl radical;

a radical —$COOZ_5$ or a radical with $Z_5$ and $Z_6$ selected, independently of one another, from a hydrogen atom and a $C_1$-$C_6$ alkyl radical;

a —CN function;

it being understood that two adjacent radicals selected from $R_1$ to $R_5$ or from $R_6$ to $R_{10}$ can together form a ring selected from the group comprising phenyl, naphthyl, furanyl, thiophenyl, pyrrolyl and triazolyl;

$X_1$ to $X_{12}$ represent, independently of one another, a carbon atom or a nitrogen atom;

$Y_1$ and $Y_2$, represent, independently of one another:
a hydrogen atom or a halogen atom;
a $C_1$-$C_6$ alkyl radical or a $C_3$-$C_{10}$ aryl radical,
a radical —O—$Z'_1$ with $Z'_1$ selected from the group comprising a hydrogen atom, a $C_1$-$C_6$ alkyl radical, a $C_2$-$C_6$ acyl radical and a $C_3$-$C_{10}$ aryl radical;
a radical with $Z'_2$ and $Z'_3$ selected, independently of one another, from the group comprising a hydrogen atom, an oxygen atom, a nitrogen atom, a $C_1$-$C_6$ alkyl radical, a $C_2$-$C_6$ acyl radical and a $C_3$-$C_{10}$ aryl radical;

a radical —$COOZ'_4$ or a radical with $Z'_4$ selected from the group comprising a hydrogen atom and a $C_2$-$C_6$ acyl radical and $Z'_5$ selected from the group comprising a hydrogen atom, a $C_2$-$C_6$ acyl radical and a $C_3$-$C_{10}$ aryl radical;

a —CN function;

Z represents an oxygen atom or a chain —$NZ_7$—, with $Z_7$ selected from the group comprising a hydrogen atom, a $C_1$-$C_6$ alkyl radical and a $C_3$-$C_{10}$ aryl radical;

$W_1$ and $W_2$ represent, independently of one another:
a hydrogen atom;
an —$NO_2$, —$N_3$ or —CN function;
a radical —$COOZ''_1$ or a radical with $Z''_1$ selected from the group comprising a hydrogen atom and a $C_1$-$C_6$ alkyl radical and $Z''_2$ selected from the group comprising a hydrogen atom, a $C_1$-$C_6$ alkyl radical and a $C_3$-$C_{10}$ aryl radical; their (R,S) enantiomers and their pharmaceutically acceptable salts, for use for the prevention and/or treatment of disorders caused by poisoning with ciguatoxins; the present invention also relates to the use of the compounds as defined above for preparing a pharmaceutical composition intended for the prevention and/or treatment of disorders caused by poisoning with ciguatoxins.

The compounds of general formula (I) according to the present invention are notably used after being isolated for example from plant extracts; they can also be obtained isolated after chemical synthesis.

"Halogen atom" means the chemical elements of group VII of the periodic table of the elements, notably fluorine, chlorine, bromine and iodine.

"$C_1$-$C_6$ Alkyl radical" means a linear or branched hydrocarbon radical with from 1 to 6 carbon atoms.

"$C_2$-$C_6$ Acyl radical" means a radical comprising 2 to 6 carbon atoms, R being an alkyl chain with m carbon atoms, m between 0 and 4, and R' an alkyl radical with n carbon atoms, n between 1 and 5, and such that m+n is between 1 and 5. Alkyl chain or radical means a linear or branched hydrocarbon chain or radical, respectively.

"$C_3$-$C_{10}$ Aryl radical" means a mono- or bicyclic aromatic radical with from 3 to 10 carbon atoms. Preferably the $C_3$-$C_{10}$ aryl radicals are selected from the group comprising the pyrrole, thiophene, furan, oxazole, isoxazole, thiazole, imidazole, pyrazole, pyridinyl, pyrimidinyl, guanyl, naphthyl, quinoleinyl, indolyl, benzofuranyl, benzothiophenyl radicals.

"Glycosyl radical" means a monomer or dimer of glycosyl, mannosyl, glucuronyl, glucosamine and mannosamine residues.

Preferably, the compounds of general formula (I) are such that:

$X_1$ to $X_{12}$ represent a carbon atom; and/or $Y_1$ and $Y_2$ represent a hydrogen atom.

A compound of general formula (I) preferred according to the invention is rosmarinic acid.

Rosmarinic acid ((R)-a-[[3-(3,4-dihydroxyphenyl)-1-oxo-2E-propenyl]oxy]-3,4-dihydroxybenzenepropanoic acid, molecular weight 360 and empirical formula $C_{18}H_{16}O_8$) is a polyphenolic compound of structure:

Rosmarinic acid

The chemical synthesis of rosmarinic acid was described by Zinsmeister (Zinsmeister H. D. et al., 1991, Angew. Chem. 103, 134-151).

Rosmarinic acid can also be produced by a biotechnological method of culture of plant cells (Hippolyte et al., 1992, 1. Plant Cell Rep. 11, 109-112) or can be isolated from plants (Lu et al., 1999. Phytochemistry 51, 91-94; Zgorka et al. 2001. J. Pharmaceut. Biomed. 26, 79-87).

This compound is known to have biological activities of interest: antiviral, antibacterial, anti-inflammatory and antioxidant (Petersen et al., 2003, Phytochemistry 62, 121-125); it is commonly used in the food and cosmetic industries. However, it has never been described as being likely to have a beneficial effect on food poisoning such as ciguatera.

The compounds of general formula (I) can be synthesized by coupling of the peptide type (production of ester and amide analogs) between carboxylic acid units and alcohol/amine units as described by See-Hyoung Park et al. (*Bioorganic and Medicinal Chemistry Letters* 2003, 12 (20), 3455-3459).

The disorders caused by poisoning with ciguatoxins are of several kinds:

Digestive disorders: These are the first to appear; they can be isolated or also associated with nervous signs. The symptoms most often encountered are diffuse abdominal pains, nausea and vomiting, and diarrhea, most often watery. Other symptoms can occur such as tenesmus and hiccups.

Disorders of the central and/or peripheral nervous system: They appear in a few days, or even in a few hours, and are the signs that may persist longest (weeks, sometimes months). They may affect the entire nervous system.

The neurological signs relating more particularly to the central nervous system include cerebellar syndromes (a cerebellar ataxia may be observed with problems of coordination and balance), disorders of the central nervous system, chronic fatigue (asthenia, lethargy, sleep disorders with nightmares, early morning waking, exercise intolerance, lack of motivation, various pains etc.), headaches, vertigo, dizziness, visual or auditory hallucinations.

Those affecting the peripheral nervous system most often include paresthesias (tingling, numbness, formication) which are observed in particular at the extremities and the face (perioral, labial, lingual, pharyngeal); dysesthesias, which are also frequent and regarded as one of the signs most suggestive of ciguatera: the patient complains of sensations of burning or of electric discharges on contact with cold objects; we may also mention ataxia.

Other signs linked to neurological disorders may be observed: swallowing disorders, convulsions, consciousness disorders, coma, paralysis of respiratory function.

Cardiovascular disorders: These are usually regarded as the most serious aspect of the intoxication. When present, they occur early but they rarely last more than a week. The following are observed most often: a sinus bradycardia below 60/min, arterial hypotension, orthostatic hypotension that may persist for up to four weeks.

Musculoskeletal disorders: Among these, we may mention: myalgias, arthralgias (especially of the large joints, particularly the knees, ankles, shoulders and elbows).

Skin disorders: Pruritus is one of the main symptoms of ciguatera, to such an extent that it has given its name to the disease in New Caledonia: la gratte ("scratching"). The palms of the hands and the soles of the feet are the most often affected. Pruritus can sometimes be generalized, notably after ingestion of alcohol or following strenuous physical exercise, i.e. when the cutaneous blood flow is increased. The itching can be very severe and may cause lesions from scratching with their range of complications: excoriations, abscesses, cellulitis, scarring, lichenification.

Other skin disorders may be observed such as skin eruptions: nonspecific papuloerythematous eruptive lesions, sometimes with desquamation during the healing phase.

Thus, the compounds and/or the pharmaceutical compositions according to the invention are more particularly intended for treating diffuse abdominal pains and/or nausea and vomiting and/or diarrhea and/or a cerebellar syndrome and/or chronic fatigue and/or headaches and/or vertigo and/or dizziness and/or visual or auditory hallucinations and/or paresthesias and/or dysesthesias and/or swallowing disorders and/or convulsions and/or consciousness disorders and/or coma and/or paralysis of respiratory function and/or sinus bradycardia below 60/min and/or arterial hypotension and/or orthostatic hypotension and/or myalgias and/or arthralgias and/or pruritus and/or skin eruptions.

The amount of compound of general formula (I) and notably of rosmarinic acid to be administered to the mammal depends notably on the severity of the disease and the symptoms to be treated, notably resulting from the amount of ciguatoxin absorbed and the route by which it was absorbed, and finally it depends on the age and the weight of the individual to be treated. As rosmarinic acid is of low toxicity, it can be administered at high concentration. As a nonlimiting example, the daily dose of rosmarinic acid or of a derivative thereof is between 0.1 mg and 1 g, preferably between 5 and 500 mg, taken in 1 to 3 divided doses.

The pharmaceutical composition comprising a compound of general formula (I) can be adapted for administration by the oral, parenteral, pulmonary, ocular, nasal route etc.

The present invention will be better understood from the rest of the description hereunder, which refers to examples of isolation and characterization of rosmarinic acid as active principle of *H. foertherianum* and evaluation of its activity against the effects of ciguatoxins; as well as the appended drawings in which:

DRAWINGS

FIG. 1 is a graph showing the cellular viability of neuroblastomas in the presence of ciguatoxins contained in samples of toxic giant clam (GPS59) at 100 μg/ml with or without rosmarinic acid (in a range from 10 to 1000 μg/ml).

FIG. 2 is the curve of competition between the radioligand ([$^3$H]—PbTx-3) and rosmarinic acid on the sodium channels of a preparation of rat brain membranes. This curve shows the displacement of the labeled brevetoxin [$^3$H]PbTx-3 from its site of action by the rosmarinic acid.

However, obviously these examples are given purely to illustrate the object of the invention and in no way constitute a limitation thereof.

EXAMPLE

I. Isolation of the Product

The active principle of *H. foertherianum* was isolated by bioguided chemical fractionation.

Yellowed leaves of *H. foertherianum* were collected at the foot of a tree in the coastal region of New Caledonia (Anse Vata, Nouméa). The remedy is prepared according to the method usually employed (Laurent et al., 1993). Briefly, 200 g of yellowed leaves are boiled in 1 liter of water for 30 minutes. The solution (about 750 ml) is then filtered and lyophilized to give 7.934 g of raw extract. 7.8 g is then dissolved in water again and partitioned with n-butanol. 500 mg of the butanolic phase is chromatographed on a silica column and eluted with 6 mixtures of dichloromethane and of methanol of increasing polarity. The active principle (about 360 mg) is eluted principally (90%) with $CH_2Cl_2/MeOH$.

II. Analysis of the Product

Structural analysis of the product is performed by proton and carbon NMR using a Brucker ARX400 spectrometer. The mass spectrum is obtained on a Perkin Elmer API Sciex triple quadrupole spectrophotometer equipped with electrospray.

The compound was identified as being rosmarinic acid by comparing the mass spectrum and NMR data with those of a control compound and those in the literature.

III. Toxicity of Rosmarinic Acid

The LD50 of rosmarinic acid was determined after injection of a solution at 531 mg/kg intravenously (i.v.) in the mouse (Fiche Sigma-Aldrich, value taken from Petersen, 2003. Reference: Parnham, M. J., Kesselring, K., 1985. Rosmarinic acid. Drugs of the Future 10, 756-757.

It is clear from these results that at this concentration, rosmarinic acid does not display toxicity.

IV. Activity of Rosmarinic Acid

IV.1. Inhibition of the Cytotoxicity Caused by Extracts of Toxic Loach or of Toxic Giant Clams on Neuroblastoma Cell Cultures The sample of salmon-pink loach (Ref15), supplied by the Louis Malardé Institute, was collected at Mururoa (Tuamotu Archipelago, French Polynesia). The sample of giant clam (GPS59) was collected at Raivavae (Austral Islands, French Polynesia). The toxicity of these two samples was confirmed beforehand on mice, by a cytotoxicity assay on neuroblastomas and radioligand assays with P-CTX-3.

The samples are stored at 4° C. The rosmarinic acid was obtained from Sigma.

96-well plates are prepared with 50 000 cells in 100 μL of medium per well. The outer wells are not used, to avoid variations of response due to edge effects. The cells are incubated for 24 h at 37° C. with 5% $CO_2$ to give them time to adhere.

A mixture of ouabain (cardiac glycoside involved in cellular permeability, inhibiting the Na/K pump) and veratridine (polycyclic alkaloid which leads to persistent activation of the sodium channels), designated O/V hereinafter, in which the two active substances are present respectively at a final concentration of 0.33 and 0.033 mM in 20 μl, is added to the wells.

Ouabain is an inhibitor of ATPase $Na^+/K^+$, and veratridine is an activator of the sodium channels. The combined action of these two products induces a raised intracellular level of sodium and causes a change in the morphology of the cells, which greatly reduces their viability. The induction, by these two compounds, of sensitization to the toxins acting on the sodium channels makes it possible to visualize the cytotoxicity of the toxins.

Then the extracts of loach (LST) or of giant clam (GSP), dissolved beforehand in culture medium at the desired concentration (final concentration per well of 250, 125 and 100 μg/ml) are added, and finally rosmarinic acid is added at various concentrations (final concentration per well between 10 and 1000 μg/ml). Each well is made up to a final volume of 200 μl with the culture medium.

All the plates have a standard control of culture medium (cells only) and a control with cells in the presence of the O/V mixture. Rosmarinic acid is tested alone with the O/V mixture to record effects of cytotoxicity or of cellular proliferation as well as any interferences of coloration due to strong concentrations of products, which can lead to false positives in spectrophotometer readings.

Each sample is tested in triplicate with and without rosmarinic acid but always in the presence of the O/V mixture.

The cells are thus incubated at 37° C. and 5% $CO_2$ for 18 h.

After incubation, the medium is removed from the wells and the plate is left to dry on absorbent paper for carrying out the assay with MethylThiazolyldiphenyl-Tetrazolium (MTT) bromide.

The MTT assay is based on the capacity of the enzymes (mitochondrial succinate dehydrogenases) of the viable cells to convert the yellow salt of tetrazolium to formazan crystals, which are insoluble in PBS. A solution of MTT at 0.8 mg/ml is prepared in PBS (phosphate-buffered saline); 50 μl of this solution is added to each well.

After incubation for 1.5 h, the formazan crystals that formed are dissolved with 150 μL of DMSO (dimethylsulfoxide) for each well. After homogenization, the plates are read with a UV plate reader at 490 nm. Then the data are transferred and processed using Excel® and analyzed with the GraphPad Prism® software (version 4).

Figure 1:
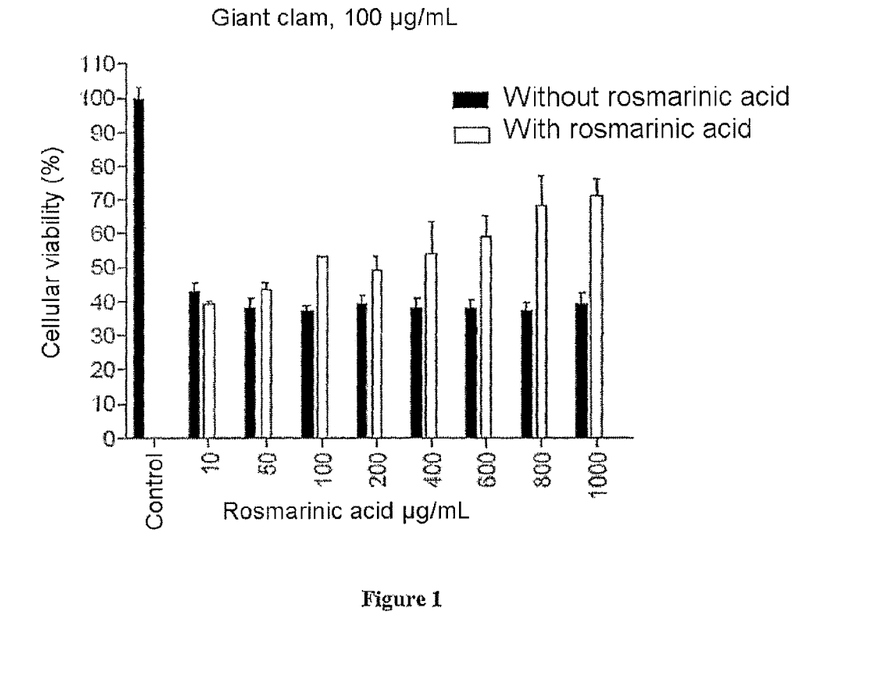

The graph in FIG. 1 shows the cytotoxicity measured by the cellular viability of an extract of toxic giant clam (GPS59) at 100 μg/ml with or without rosmarinic acid at different concentrations (10 to 1000 μg/ml). This graph clearly shows the protective effect of rosmarinic acid; the effect of this compound significantly increases cellular viability starting from 50 μg/ml. Similar results were observed with the extract of toxic salmon-pink loach.

On the basis of these results, it can be estimated that the IC50 of rosmarinic acid (concentration of rosmarinic acid for 50% decrease in cellular mortality caused by ciguatoxins and associated toxins) is between 0.5 and 1 mg/ml.

IV.2. Displacement of Labeled Brevetoxin [$^3$H]PbTx-3 from its Site of Action (Voltage-Dependent Sodium Channels)

Rat brain synaptosomes are prepared as previously described by Dechraoui et al. (1999, Toxicon. 37(1):125-43). The protein concentration of the synaptosomal preparations is determined in duplicate by Bradford's method with bovine serum albumin as standard (Bradford, M. M., 1976, Anal. Biochem. 72: 248-254).

The final protein concentration is of the order of 120 μg/ml.

After incubation of these preparations with the tritiated brevetoxin [$^3$H]PbTx-3, a maximum of 10% of the total radioactivity is observed.

The test for detection of ligand-receptor interaction is performed in a tube with a final concentration of tritiated brevetoxin [$^3$H]PbTx-3 of 1.1 nM, following the protocol of Darius et al. (Darius et al., 2007 *Toxicon* 50(5), 612-626). The radioactivity is determined using a Perkin Elmer Microbeta Trilux 1450 scintillation counter in counting flasks of 2 ml of a Betaplate scintillation liquid (Perkin Elmer).

The nonspecific interaction is evaluated by measuring the radioactivity in the presence of a saturating concentration of [$^3$H]PbTx-3 (0.67 mM) and is subtracted from the total interaction to give the specific interaction.

The ciguatoxin P-CTX-3C (obtained from a clonal culture of *Gambierdiscus polynesiensis*) is known to display a better affinity at the site of action than the brevetoxins; it was used as internal standard for sample calibration (Chinain et al., 1999; Darius et al., 2007).

Two tubes of quality controls of the radioligand experiments are used for each experiment; they are composed of a toxic extract of *Gambierdiscus polynesiensis* with a known concentration of ciguatoxin P-CTX-3C equivalent to 3.1 pg.

Eight dilutions in duplicate were tested using 2 concentrations of rosmarinic acid at 5 and 20 mg/ml.

The sigmoidal curves and the $IC_{50}$ values are obtained using Graphpad Prism v4.0 software. The $IC_{50}$ is defined as the concentration of extract capable of inducing 50% inhibition of interaction with [$^3$H]PbTx-3 and it is expressed in mg equivalent/ml of extract.

Figure 2:
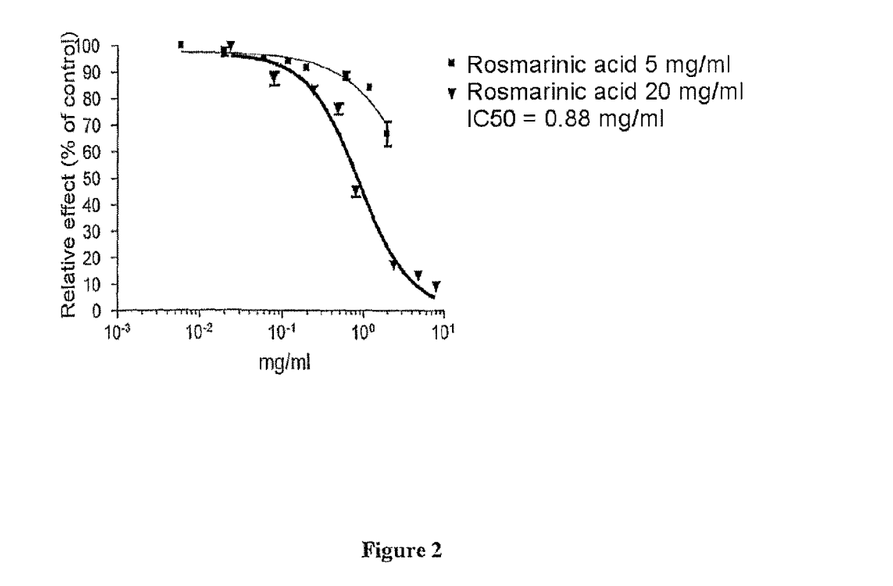

FIG. 2 shows the curve of competition between the radioligand ([$^3$H]—PbTx-3) and rosmarinic acid for the sodium channels of a preparation of rat brain membranes. In the presence of rosmarinic acid at 5 and 20 mg/ml, we find a decrease in the measured radioactivity, indicating replacement of the tritiated brevetoxin on the sodium channels by rosmarinic acid.

The value of IC50 can thus be calculated: 0.88 mg/ml and the value of Ki is $1.43 \times 10^{-3}$ M V. Estimation of the Amount of Active Principle Ingested by a Person During Treatment with the Traditional Remedy The level of rosmarinic acid is estimated at 1.2 mg/g of fresh leaves of *Heliotropium foertherianum*; i.e. for leaves of about 10 grams, approximately 12 mg of rosmarinic acid and for a remedy based on a decoction from 4 to 5 leaves, approximately 50 mg of said product.

This value is just a guide, as the posology of a traditional remedy is very variable; moreover, the content of active substance in the remedy can also vary depending on whether coastal or inland plants are used.

The invention claimed is:

1. A method for preventing or treating a disorder caused by poisoning with ciguatoxins in a subject comprising administering to a subject in need thereof a pharmaceutical composition consisting essentially of isolated Rosmarinic acid.

2. The method of claim 1, wherein the ciguatoxins are selected from Pacific ciguatoxins or P-CTX-1 to 23, the Caribbean ciguatoxins or C-CTX-1 to 12 and the Indian Ocean ciguatoxins or I-CTX-1 to 4.

3. The method of claim 1, wherein said disorder caused by poisoning with ciguatoxins is a digestive disorder, a disorder of the central or peripheral nervous system, a cardiovascular disorder, a musculoskeletal disorder, or a skin disorder.

4. The method of claim 1, wherein said disorder is a diffuse abdominal pain, nausea and vomiting, diarrhea, a cerebellar syndrome, chronic fatigue, a headache, vertigo, dizziness, a visual or auditory hallucination, paresthesias, dysesthesias, a swallowing disorder, a convulsion, a consciousness disorder, coma, paralysis of respiratory function, sinus bradycardia below 60/min, arterial hypotension, orthostatic hypotension, myalgias, arthralgias, pruritus, or a skin eruption.

5. The method of claim 1, wherein the subject is administered a daily dosage amount between 0.1 mg and 1 g, taken in 1 to 3 divided doses.

6. The method of claim 1, wherein the isolated rosmarinic acid is comprised in a pharmaceutical composition suitable for administration by the oral, parenteral, pulmonary, ocular, or nasal route.

7. The method of claim 1, wherein the subject has a disorder caused by poisoning with ciguatoxins.

8. The method of claim 7, wherein said disorder is ciguatera.

\* \* \* \* \*

UNITED STATES PATENT AND TRADEMARK OFFICE
CERTIFICATE OF CORRECTION

PATENT NO. : 9,060,985 B2  
APPLICATION NO. : 13/388029  
DATED : June 23, 2015  
INVENTOR(S) : Laurent et al.

Page 1 of 1

It is certified that error appears in the above-identified patent and that said Letters Patent is hereby corrected as shown below:

On the title page, item [75]

Mireille Chinain, replace "Tahiti (FR)" with --Pirae, Tahiti (PF)--.

Taiana Darius, replace "Tahiti (FR)" with --Pirae, Tahiti (PF)--.

Shilpa Kumar-Roine, replace "New Caledonia (FR)" with --Noumea (NC)--.

Signed and Sealed this  
Nineteenth Day of July, 2016

Michelle K. Lee  
*Director of the United States Patent and Trademark Office*